(12) United States Patent
Voisine (10) Patent No.: US 10,371,739 B2
(45) Date of Patent: Aug. 6, 2019

(54) ARRANGEMENT FOR DETECTING A METER MAINTENANCE CONDITION USING WINDING RESISTANCE

(71) Applicant: Landys+Gyr LLC, Lafayette, IN (US)

(72) Inventor: John T. Voisine, Lafayette, IN (US)

(73) Assignee: Landis+Gyr LLC, Lafayette, IN (US)

( * ) Notice: Subject to any disclaimer, the term of this patent is extended or adjusted under 35 U.S.C. 154(b) by 565 days.

(21) Appl. No.: 14/928,995

(22) Filed: Oct. 30, 2015

(65) Prior Publication Data

US 2017/0122995 A1     May 4, 2017

(51) Int. Cl.
   *G01R 31/04*     (2006.01)
   *G01K 7/16*     (2006.01)
   (Continued)

(52) U.S. Cl.
   CPC ............. *G01R 31/041* (2013.01); *G01K 7/16* (2013.01); *G01N 25/72* (2013.01);
   (Continued)

(58) Field of Classification Search
   CPC ............ G01K 13/00; G01K 7/16; G01K 7/00; G01K 7/24; G01K 7/36; G01K 2217/00;
   (Continued)

(56) References Cited

U.S. PATENT DOCUMENTS 3,244,980 A * 4/1966 Jung ...................... G01R 21/04
                                                            324/106
4,167,115 A * 9/1979 Stoever ...................... G01F 1/20
                                                            73/861.05

(Continued)

FOREIGN PATENT DOCUMENTS

CA          2689531 A1 * 1/2009 ........... G01R 31/346
JP          10221397 A * 8/1998
JP          2003090851 A * 3/2003
JP          3711299 B2 * 11/2005 ............... H02H 5/04

OTHER PUBLICATIONS

Deng X ; Huang K ; Song J ; Tan G ; Wang L ; Wang R: "Synchronous motor winding of resistance and temperature monitoring device, has direct current (DC) current sensor", CN202066912U. p, Dec. 2011 (Year: 2011).*
International Search Report for PCT/US2016/059558, dated Feb. 14, 2017.

*Primary Examiner* — Gail Kaplan Verbitsky
(74) *Attorney, Agent, or Firm* — Kilpatrick Townsend & Stockton LLP (57) ABSTRACT

An arrangement for use in a utility meter is disclosed. The arrangement includes a meter blade coupled to a current coil. The arrangement further includes a current sensor that includes a winding about a core. The current sensor is in a current sensing relationship with the current coil. The winding has a resistance that varies as a function of temperature. The arrangement further includes a processing circuit that is operably coupled to receive a measurement signal from the winding. The processing circuit is configured to determine a DC component of the measurement signal, determine the resistance of the winding based at least in part on the determined DC component, and cause a value representative of the determined resistance to be displayed or communicated to an external device.

19 Claims, 6 Drawing Sheets

(51) Int. Cl.
*G01N 25/72* (2006.01)
*G01R 21/00* (2006.01)
*G01R 31/06* (2006.01)

(52) U.S. Cl.
CPC .......... *G01K 2217/00* (2013.01); *G01R 21/00* (2013.01); *G01R 31/06* (2013.01)

(58) Field of Classification Search
CPC ........... H01L 21/67248; H01L 41/1132; G01R 19/2513; G01R 27/08; G01R 13/02; G01R 21/00; H01F 38/32; G01N 25/72
USPC ................ 374/152, 153, 141, 185, 163, 183
See application file for complete search history.

(56) References Cited

U.S. PATENT DOCUMENTS

| | | | | |
|---|---|---|---|---|
| 4,933,633 A * | 6/1990 | Allgood | ................ | G01F 1/684 324/116 |
| 5,066,904 A | 11/1991 | Bullock | | |
| 5,708,336 A | 1/1998 | Eyerly | | |
| 5,811,965 A * | 9/1998 | Gu | ................ | G01R 15/18 324/117 R |
| 5,949,231 A * | 9/1999 | Lau | ................ | G01R 15/185 324/117 R |
| 6,023,160 A * | 2/2000 | Coburn | ................ | G01R 1/203 324/126 |
| 6,618,684 B1 * | 9/2003 | Beroset | ................ | G01R 11/185 702/99 |
| 6,954,060 B1 * | 10/2005 | Edel | ................ | G01R 15/183 324/117 R |
| 7,245,126 B1 * | 7/2007 | Hasegawa | ................ | G01R 33/31 324/315 |
| 7,427,856 B2 * | 9/2008 | Jones | ................ | G01R 15/185 324/117 R |
| 7,683,795 B2 * | 3/2010 | Bjorn | ................ | G01R 15/246 324/96 |
| 7,805,262 B2 * | 9/2010 | Slater | ................ | G01K 13/00 702/61 |
| 7,821,753 B2 * | 10/2010 | Evans | ................ | H02H 9/001 361/90 |
| 9,310,404 B2 * | 4/2016 | Takei | ................ | G01R 21/04 |
| 2007/0107973 A1 * | 5/2007 | Jiang | ................ | B62D 5/046 180/443 |
| 2008/0117014 A1 * | 5/2008 | Waeckerle | ................ | H01F 1/15308 336/234 |
| 2008/0157751 A1 * | 7/2008 | Jones | ................ | G01R 15/185 324/127 |
| 2009/0072813 A1 * | 3/2009 | Banhegyesi | ................ | G01R 15/183 324/127 |
| 2010/0321964 A1 * | 12/2010 | Brinlee | ................ | H02M 3/33507 363/21.18 |
| 2011/0071771 A1 | 3/2011 | Viale | | |
| 2014/0285180 A1 | 9/2014 | Foote | | |
| 2014/0333290 A1 * | 11/2014 | Boudreau, Jr. | ................ | G01R 15/181 324/123 R |
| 2015/0349652 A1 * | 12/2015 | Lefedjiev | ................ | H02M 3/33523 363/21.14 |
| 2015/0377949 A1 * | 12/2015 | Ramirez | ................ | G01R 22/068 361/103 |
| 2016/0341773 A1 * | 11/2016 | Reineccius | ................ | G01R 22/06 |
| 2017/0016943 A1 * | 1/2017 | Martin | ................ | G01R 22/10 |
| 2017/0184458 A1 * | 6/2017 | Jefferies | ................ | G01K 7/16 |
| 2017/0194870 A1 * | 7/2017 | Werner | ................ | H02M 3/33523 |
| 2018/0080970 A1 * | 3/2018 | Kraus | ................ | G01R 31/04 |

* cited by examiner

ARRANGEMENT FOR DETECTING A METER MAINTENANCE CONDITION USING WINDING RESISTANCE

FIELD OF THE INVENTION

The present invention relates generally to utility meters, and more particularly, to electricity meters that includes electrical contacts that are subject to wear.

BACKGROUND OF THE INVENTION

Electricity meters that measure energy consumption or power consumption typically connect between a utility power line and a load. For example, an electricity meter for a residential customer is often connected at the point at which the electrical system of the residence connects to the utility line. The meter may thereby perform measurements regarding the energy consumed by the load.

Utility meters often include one or more electrical contacts across which a significant amount of current flows. For example, meters often have blades that connect across the power line to enable the measurement of load current and load voltage from within the meter. The blades are received by the jaws of a meter mounting device of the building. The jaws use spring compression to retain the blades securely. If the meter is to be replaced or repaired, the meter may be pulled out of the mounting device, and hence the blades out of the jaws. Although the blades and jaws are usually mechanically robust, they are nevertheless subject to wear, and possibly corrosion. This is particularly the case if the meter has been removed or replaced several times. If wear on the jaws is significant, or if the jaws have corrosion, then there is a possibility of introducing a non-trivial resistance at the jaw/blade connection, which is undesirable. Similarly it is possible for the spring used to effect jaw compression to lose some force with aging or heating over time resulting in a reduction of jaw compression force.

Likewise, certain meters have switches that allow for disconnection of electrical service to a load. For example, many meters allow for remote switching off of the load. Such switches necessarily must have substantial contacts because they carry the entire current of the load when the switch is closed. If these switches are used with some frequency, then there is a potential for degradation. Degradation of the switch contacts increases the resistance over the switch contacts. Such resistance creates additional power loss within the meter, which is undesirable.

Because it is undesirable to introduce resistance at the meter/socket connections or service switch connections, there is a need for a way to detect possible degradation of such connections over time.

SUMMARY OF THE INVENTION

At least some embodiments of the present invention addresses the above-stated needs, as well as others, by using meter circuitry to detect a possible temperature rise in meter contacts by measuring the resistance in the windings of a sensor within the meter. The corresponding method and apparatus may be implemented using many components already present for purposes of performing energy metering.

In one embodiment, a method determines temperature information associated with a current coil connection in a meter. The method includes conveying heat from a current coil connection to a location proximate a winding disposed about a core. The core includes an opening through which a current carrying coil is disposed, the current carrying coil carrying current measured by the meter. The method also includes measuring a resistance of the winding disposed about a core, wherein the winding has a resistance that varies as a function of temperature. The method includes determining a temperature value based on the measured resistance and storing or communicating the determined temperature value.

Another embodiment is an arrangement for use in a utility meter that includes, a meter blade coupled to a current coil, a current sensor, and a processing circuit. The current sensor includes a winding around a core. The current sensor is in a current sensing relationship with the current coil. The winding has a resistance that varies as a function of temperature. The processing circuit is operably coupled to receive a measurement signal from the winding. The processing circuit is configured to determine a DC component of the measurement signal, determine the resistance of the winding based at least in part on the determined DC component, and store or communicate a value representative of the determined resistance.

The above-described embodiments both obtain a temperature value or a resistance value which can be used to evaluate whether there is an issue with a current coil connection. The current coil connection may be a meter blade/jaw connection, or service switch contacts, among other things.

The above described features and advantages, as well as others, will become more readily apparent to those of ordinary skill in the art by reference to the following detailed description and accompanying drawings.

DETAILED DESCRIPTION

Figure 1:
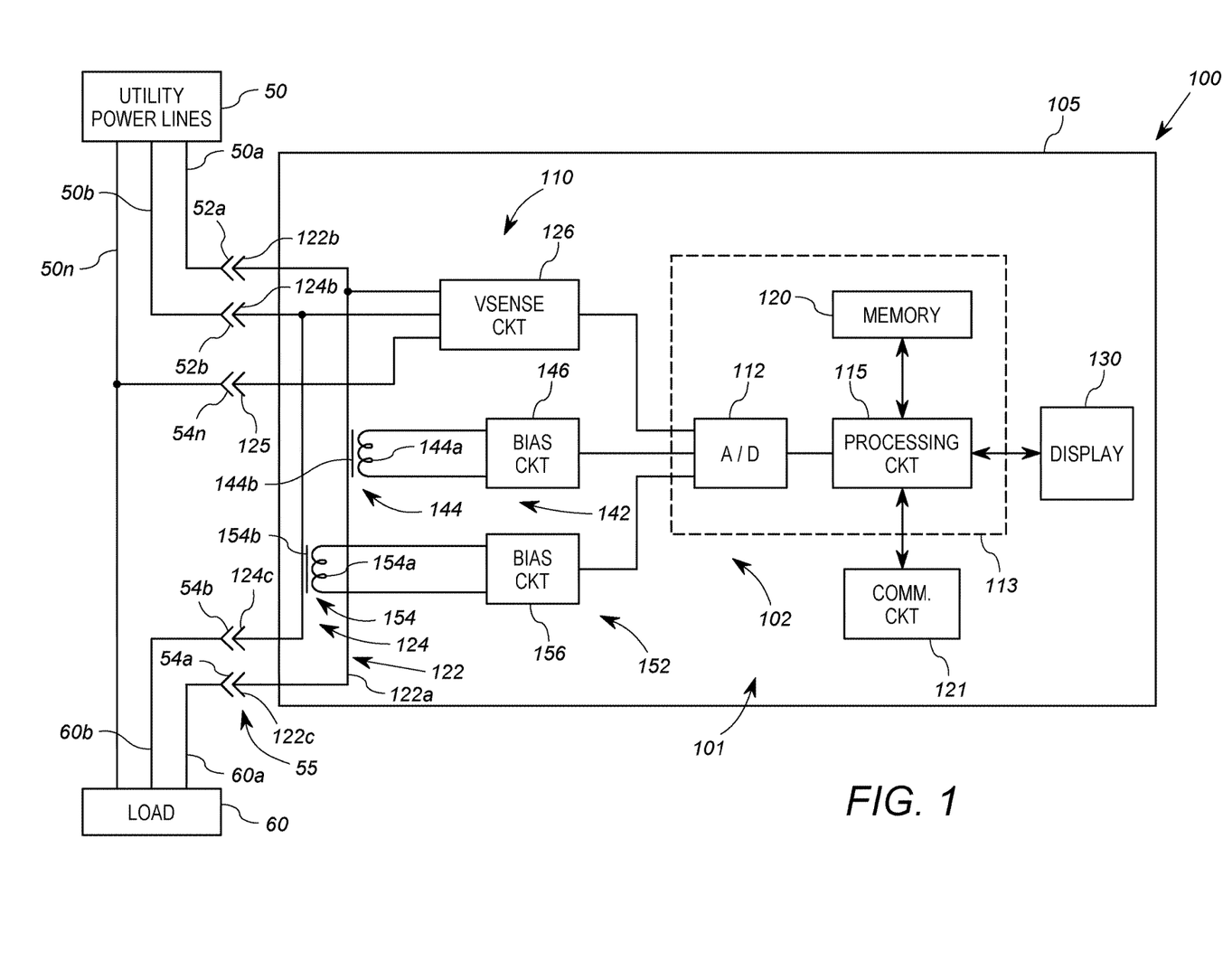
FIG. 1 shows a schematic block diagram of an electricity meter that includes an exemplary arrangement for determining temperature information associated with a current coil connection according to a first embodiment of the invention.

FIG. 1 shows a schematic block diagram of an electricity meter 100 that includes an exemplary arrangement 101 for determining temperature and/or resistance information associated with a current coil connection according to a first embodiment of the invention. In general, the electricity meter 100 is configured to generate measurements of energy and/or power delivered from utility power lines 50 to a load 60. The power lines 50 are coupled to the load 60 through the meter 100 as will be discussed further below. In this embodiment, the power lines 50 include first and second power lines 50a, 50b of a two phase service (often called a "network service"), which further includes a neutral line 50n. It will be appreciated, however, that the arrangement 101 discussed herein may readily be adapted to meters that connect to various other standard power line configurations associated with standard electrical service, including but not limited to multiphase electrical service and single phase residential services.

The power lines 50a, 50b connect to a meter mounting device or socket 55 having a plurality of jaws 52a, 52b, 54a, 54b and 54n. Specifically, the power lines 50a, 50b are electrically coupled to the jaws 52a, 52b, and the neutral line 50n is electrically coupled to the jaw 54n. The jaws 54a, 54b are electrically coupled to the feeder lines 60a, 60b of the load 60. The neutral line 50n is also coupled to the load 60. The jaws 52a, 52b, 54a, 54b and 54n are strongly spring-loaded conductive receptacles that are configured to receive meter blades, discussed further below, and may suitably be conventional meter socket jaws.

The meter 100 includes a housing 105 in which are disposed a metrology circuit 102, at least one memory 120, a communication circuit 121 and a display 130. The meter 100 also includes first and second current coils 122 and 124 supported on and partially within the meter housing 105. The metrology circuit 102 includes a sensor circuit 110, an A/D conversion unit 112, and a processing circuit 115. It will be appreciated that in the exemplary embodiment, the processing circuit 115 is part of a commercially available chip package 113 that includes the A/D conversion unit 112, the memory 120, and/or other support devices. The housing 105 may take any suitable form, and is generally configured to withstand a wide range of environmental conditions. The housing 105 also provides at least some protection against environmental conditions to the various elements disposed therein. Suitable housings for utility meters are well-known in the art.

The first current coil 122 includes a body 122a of conductive metal, such as a copper bar, that terminates at either end in current blades 122b, 122c. When the meter 100 is properly installed in the meter mounting device 55, the current blade 122b is received by the jaw 52a, and the current blade 122c is received by the jaw 54a. Thus, electricity may flow from the utility power line 50a to the load 60 via the jaw 52a, the current coil 122, the jaw 54a, and the feeder line 60a. The blades 122b, 122c are generally disposed external to the housing 105, while the body 122a of the current coil 122 extends through the interior of the housing 105.

Similarly, the first current coil 124 includes a body 124a of conductive metal, such as a copper bar, that terminates at either end in current blades 124b, 124c. When the meter 100 is properly installed in the meter mounting device 55, the current blade 124b is received by the jaw 52b, and the current blade 124c is received by the jaw 54b. Thus, electricity may flow from the utility power line 50b to the load 60 via the jaw 52b, the current coil 124, the jaw 54b, and the feeder line 60b. The blades 124b, 124c are generally external to the housing 105, while the body 124a of the current coil 124 extends through the interior of the housing 105.

The sensor circuit 110 in this embodiment includes a voltage sensor circuit 126 and current sensors 142, 152 that are operably coupled to detect voltage and current signals representative of voltage and current provided to the load 60, and to generate measurement signals therefrom. In particular, the measurement signals generated by the sensor circuit 110 are analog signals having respective waveforms representative of the voltage and current provided to the load. To this end, the voltage sensor circuit 126 may suitably include voltage divider circuits, not shown, coupled to each of the current coils 122, 124 as well as the neutral line that is coupled into the meter via blade 125. Suitable voltage sensor circuits are of conventional design.

The current sensor 142 in this embodiment includes a current transformer 144, and a bias or conditioning circuit 146. The current transformer 144 is disposed in a current sensing relationship with the current coil 122. As will be discussed in further detail below in connection with FIG. 2, the current transformer 144 comprises a winding 144a about a core 144b. The winding 144a includes conductive wire, and has a resistance that varies as a function of temperature. In accordance with at least some embodiments of the invention, the bias circuit 146 is configured to apply a DC voltage across the winding 144a of the current transformer 144. The current transformer 144 is also operably connected through the bias circuit 146 to generate current measurement signals have a waveform that corresponds in magnitude and phase to the AC current present in the current coil 122. The bias circuit 146 is operably connected to provide the current measurement signal to the A/D conversion unit 112. Thus, the A/D conversion unit receives a current measurement signal that corresponds to the current flowing from the utility power line 50a to the load 60 through the current coil 122.

Similarly, the current sensor 152 includes a current transformer 154, and a bias or conditioning circuit 156. As with current transformer 144, the current transformer 154 comprises a winding 154a about a core 154b, and is disposed in a current sensing relationship with the current coil 124. The winding 154a has a resistance that varies as a function of temperature. In accordance with at least some embodiments of the invention, the bias circuit 156 is configured to apply a DC voltage across the winding of the current transformer 154. The current transformer 154 is also operably connected through the bias circuit 156 to generate current measurement signals having a waveform that corresponds in magnitude and phase to the AC current present in the current coil 124. The bias circuit 156 is operably connected to provide the current measurement signal to the A/D conversion unit 112. Thus, the A/D conversion unit 112 receives a current measurement signal that corresponds to the current flowing from the utility power line 50b to the load 60 through the current coil 124.

The A/D conversion unit 112 may be any suitable analog-to-digital converter that is configured to sample the analog measurement signals generated by the sensor circuit 110. The A/D conversion unit 112 is operably coupled to provide the resulting digital measurement signals to the processing circuit 115.

The processing circuit 115 includes a processing device configured to execute program instructions stored in the memory to carry out the various functions described herein, as well as other metering functions. The processing circuit 115 is operably coupled to receive the digital measurement signals from the A/D conversion unit 112 and generate energy consumption data therefrom. To this end, the processing circuit 115 includes digital processing circuitry that processes the digitized measurement signals to thereby generate the energy consumption data. Such circuits are well known in the art. As is known in the art, the processing circuit 115 may also include the functions of a controller. To this end, the processing circuit 115 also suitably includes general control and supervisory processing circuitry, not shown in detail, but which would be known to those of ordinary skill in the art. The processing circuit 115 communicates information with external devices with serial input and output ports, not shown, or communication circuits, also not shown, but which would be known to those of ordinary skill in the art.

Accordingly, the sensor circuit 110, the A/D conversion unit 112 and processing circuit 115 form the metrology circuit 102, which is configured to generate energy consumption data representative of energy used by the load. The memory 120 of the chip package 113 includes one or more storage devices of different types. The memory 120 may include volatile or non-volatile RAM, EEPROM, or other readable and/or writeable memory device, any of which may be incorporated into the integrated circuit package 113. The memory 120 stores instructions and/or parameters used by the processing circuit 115 to carry out the operations described herein, and may further store energy consumption data. In some embodiments, the memory 120 can include memory devices located external to the chip package 113.

The communication circuit 121 is operably coupled to communicate information with the processing circuit 115, as well as at least one external device. To this end, the communication circuit 121 may include an optical transceiver located at a translucent or transparent optical port, not shown. Alternatively, the communication circuit 121 may be a remote communication circuit, such as a power line modem, an RF transceiver, for example, a pager radio, or other wireless device that is capable of transmitting on a WAN, or on another wireless communication network.

Referring again to the arrangement 101 for determining temperature information associated with a current coil connection, the arrangement 101 includes the current coil 122, the current transformer 144 and the processing circuit 115. In this embodiment, the current coil connection may suitably be the connection between the meter blade 122b and the jaw 52a, or the connection between the meter blade 122c and the jaw 52b. To carry out the temperature determination, the current coil 122 in this embodiment is configured to conduct heat from the meter blade 122b and meter blade 122c to the current transformer 144. To this end, as discussed above, the current coil 122 can include a copper bar or other heat (and electrically) conductive body 122a. Thus, heat generated as a result of damaged or deteriorating connection between the meter blade 122b and the jaw 52a, or between the meter blade 122c and the jaw 54a, is conducted to the current transformer 144 by the coil body 122a. In other embodiments, the current coil connection may be the connection between the current coil 122 and a service switch within the meter, not shown, but which would be known to those ordinary skill in the art.

As discussed above, the processing circuit 115 operably coupled to receive a measurement signal from the current transformer 144 via the bias circuit 146. The processing circuit is 115 is configured to employ the measurement signal in conjunction with a voltage measurement signal received from the voltage sensor circuit 126 to generate energy consumption measurements. The processing circuit 115 is further configured to determine a DC component of the measurement signal, and to determine the resistance of the winding 144a based at least in part on the determined DC component. The processing circuit 115 is further configured to store a value representative of the determined resistance in the memory 120. The stored value may suitably be representative of the temperature of the winding 144a. As discussed above, the winding 144a has a resistance that varies as a function of a temperature. Thus, the processing circuit 115 may suitably be configured to determine a value identifying the temperature of the winding 144a based on the determined resistance of the winding 144a, and then store the determined temperature value. Because the current coil 122 conducts heat from the meter jaw connections 52a/122b and 54a/122c, any excess temperature of the winding 144a can indicate a deterioration or degradation of either or both of those meter jaw connections.

The arrangement 101 preferably further includes the current coil 124, current transformer 154 and the processing circuit 115 operating in an analogous way to determine the resistance and/or temperature in the winding 154a, which can indicate a deterioration or degradation of the meter jaw connections 52b/124b and/or 54b/124c.

The processing circuit 115 is preferably further configured to compare the stored winding temperature and/or stored winding resistance to one or more thresholds. As will be discussed below, the processing circuit 115 is configured to take certain actions depending on the results of the comparison(s).

In operation, the meter 100 is disposed within the meter mounting device 55. Under normal conditions, electricity is delivered from the power lines 50a, 50b to the load 60 through the meter 100, where the delivered energy is measured. In particular, the line voltage on the power line 50a is present on the current coil 122, and the line voltage on the power line 50b is current coil 124. In addition, the current provided to the load 60 from the power line 50a passes through the current coil 122, and the current provided to the load 60 from the power line 50b passes through the current coil 124.

The voltage sensor circuit 126 generates two voltage measurement signals VA, VB, each based on the voltage waveform present on one of the current coils 122 and 124. More specifically, the voltage measurement signal VA comprises a scaled down version of the voltage waveform on the power line 50a, which is present in the meter 100 on the current coil 122. Similarly, the voltage measurement signal VB is a scaled down version of the voltage waveform on the power line 50b, which are present in the meter 100 on the current coil 124.

The current sensor 142 generates a current measurement signal IA that has at least an AC component representative of the current delivered to the load on power line 50a via the current coil 122. Similarly, the current sensor 152 generates a current measurement signal IB that has at least an AC component representative of the current delivered to the load on power line 50b via the current coil 124. The current sensor 142 also generates the current measurement signal IA such that it either periodically or continuously includes a DC component that is a function of the resistance of the winding 144a. To this end, for example, the bias circuit 146 may periodically or continuously apply a DC voltage across the winding 144a. Exemplary circuits for doing so are discussed further below in connection with FIGS. 2 and 3. In the same manner, the current sensor 152 also generates the current measurement signal IB such that it either periodically or continuously includes a DC component that is a function of the resistance of the winding 154a.

The A/D conversion circuit 112 receives the measurement signals VA, VB, IA, IB and samples each of the signals to generate corresponding digital waveforms VAD, VBD, IAD, IBD. The processing circuit 115 obtains the digital waveforms and calculates a plurality of metering values therefrom. These values may include energy (kw-h), reactive energy (VAR-h), RMS voltage and RMS current. To this end, the processing circuit 115 preferably filters or removes from the digital current measurement signals IAD and IBD any DC component, including that purposefully added for the purpose of determining resistance/temperature of the windings 144a, 146a. To calculate energy consumption, the processing circuit 115 multiplies contemporaneous samples of VAD and IAD, sums the resulting products over time. The processing circuit 115 also performs the same operations on the contemporaneous samples of VBD and IBD are multiplied and summed. The two resulting sums, WA, WB, represent energy consumption on the respective power lines 50a, 50b by the load 60. As a consequence, the sum of WA and WB represents the total energy consumption by the load 60. It will be appreciated that various calibration factors may also be applied in the energy calculation as is known in the art.

The processing circuit 115 also performs the calculation of reactive energy (VAR-h) in a similar manner, except that that the voltage samples VAD, VBD and current samples IAD, VBD that are 90° phase shifted with respect to each other.

In accordance with at least one embodiment of the present invention, the processing circuit 115 also obtains the DC current component from the current measurement signals IAD and IBD in order to calculate the resistance and/or temperature of the respective windings IAD and IBD. Under conditions discussed further below, the DC component of the signal IAD represents the resistance of the winding 144a, and the DC component of the IBD signal represents the resistance of the winding 154a. The processing circuit 115 then stores a value representative of the resistance of the winding 144a and the resistance of the winding 154a in the memory 120.

In one embodiment, the stored values representative of the resistances of the windings 144a, 154a are the resistance values themselves. In other embodiments, the stored values are approximate temperatures of the windings 144a, 154a, which can be directly correlated to resistance. In particular, the relationship between temperature and resistance in copper is known. Thus, the processing circuit 115 may suitably convert the determined resistance values into approximate temperature values based on the temperature/resistance relationship. In some cases, the relationship between temperature and winding resistance for particular current transformers may be determined experimentally, and stored in the memory 120. The processing circuit 115 may then use that relationship (e.g. look-up table, linear function, piecewise linear equation, etc.) to determine the temperature of the windings 144a, 154a based on its resistance.

The processing circuit 115 may also cause the stored temperature values and/or resistance values to be displayed on the display 130, and/or communicated to an external device via conventional meter communication circuits, not shown, but which would be known to those of ordinary skill in the art.

The processing circuit 115 in at least one embodiment furthermore compares the determined resistance and/or temperature to a corresponding resistance or temperature threshold. In some embodiments, the processing circuit 115 only stores the value representative of the resistance of the either winding 144a, 154a when the value exceeds the threshold. For example, the processing circuit 115 is configured to compare the value representative of the resistance to a first threshold that is associated with a temperature that corresponds to a possible overheating of a blade jaw connection. If the measured resistance value exceeds the first threshold, then the processing circuit 115 stores, displays and/or communicates an indication of the event and the temperature or resistance.

The processing circuit 115 in this embodiment furthermore uses the measured resistance value to determine other anomalies or conditions in the current coils 122, 124. For example, the processing circuit 115 detects either an open winding (open circuit), or a shorted winding (short circuit) using the determined/measured resistance values. An open winding in the winding 144a or 144b will yield a very high resistance. A shorted winding will yield a very low resistance. Accordingly, the processing circuit 115 may detect whether the determined resistance of either or both windings 144a, 154a exceeds a second threshold that is much higher than the first threshold, in order to detect a possible open winding. The second threshold may be set to a value indicates a very high resistance, a resistance value likely too high to be caused by temperature of the winding alone. If the processing circuit 115 determines that the resistance is above the second, higher threshold, then the processing circuit 115 stores, displays and/or communicates an indication of a potential "open winding event". Similarly, the processing circuit 115 may detect whether the determined resistance of either or both windings 144a, 154a is below a low threshold, one that is much lower than the first threshold, and preferably one that corresponds to an impossibly low temperature, such as −100 C. This threshold would indicate that there is likely a short in the corresponding winding 144a, 154a. The processing circuit 115 may store, display and/or communicate a "shorted winding event" if the resistance value is below the low threshold.

Thus, it can be seen that the arrangement 101 of FIG. 1 can detect various potential meter issues, such as worn coil connection contacts, and the shorting or opening of a current transformer winding.

In a first exemplary scenario, it is assumed that the connection between the blade 122b and the jaw 52a is corroded and degraded, thereby exhibiting increased resistance. Because the relatively large currents going through the blade jaw connection 52a/122b, the increased resistance generates heat. The coil body 122a conducts the heat to the current transformer 144, and hence the winding 144a. The winding 144a, which has a resistance that varies as a function of temperature, exhibits an increased resistance. The bias circuit 146 and the winding 144a cooperate to convey a DC voltage component to the processing circuit 115 (via the A/D conversion unit 112) that is indicative of the resistance of the winding 144a. The processing circuit 115 determines the resistance of the winding 144a from the DC voltage component. The processing circuit 115 thereafter performs the threshold comparisons described above, and in this case determines that the resistance (or temperature if converted to temperature) exceeds the first threshold, but not the second threshold. The processing circuit 115 further determines that the resistance is not lower than the low threshold. As a result of these threshold determinations, the processing circuit 115 thus stores, displays and/or communicates a "temperature event".

In a second scenario, the winding 144a has an open circuit or has been disconnected, for example by meter tampering. When the winding 144a is open (e.g. broken or disconnected), then regardless of the condition of the blade jaw connection 122b/52a, the bias circuit 146 and the winding 144a will provide a DC voltage component indicative of an extremely high (e.g. open circuit) resistance to the processing circuit 115. The processing circuit 115 determines the resistance value from the DC voltage component, and compares the resistance value to the various thresholds discussed above. In this case, the processing circuit 115 determines that the resistance value exceeds the second threshold. As a consequence of the determination, the processing circuit 115 stores, displays and/or communicates an "open circuit event".

In a third scenario, the winding 144a has been short-circuited. When the winding 144a is shorted circuited, then regardless of the condition of the blade jaw connection 122b/52a, the bias circuit 146 and the winding 144a will provide a DC voltage component indicative of an extremely low resistance to the processing circuit 115. The processing circuit 115 will determine the resistance value from the DC voltage component, and subsequently determine that the resistance value is lower than the low threshold. As a consequence, the processing circuit 115 stores, displays and/or communicates a "short circuit event".

Figure 2:
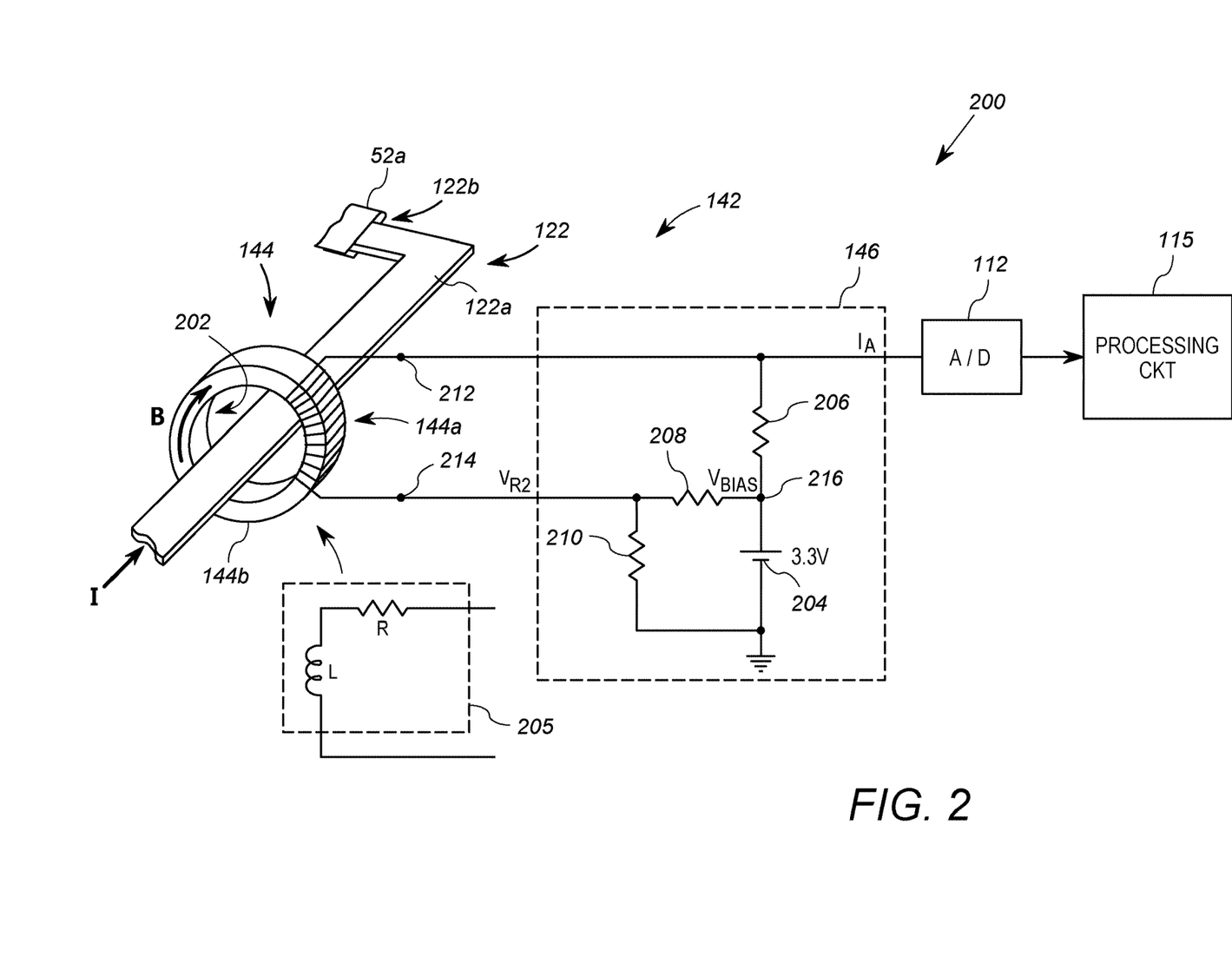
FIG. 2 shows a schematic block diagram of an arrangement for determining temperature information that may be used in the meter of FIG. 1.

FIG. 2 shows in further detail a schematic block diagram of an exemplary embodiment an arrangement 200 for monitoring a current coil connection (such as the meter jaw connection 52a/122b) that may be used as the arrangement 101 of FIG. 1. Like elements of FIGS. 1 and 2 employ like reference numbers. As shown in FIG. 2, the current transformer 144 comprises a toroid, wherein the winding 144a is wrapped about a circular core 144b. It will be appreciated that the winding 144a illustrated in FIG. 2 is merely exemplary, and that an actual winding of a current transformer for use in electricity metering will likely have at least on the order of 1000 turns. Moreover, although the term "current transformer" is commonly used to describe the winding 144a about a core 144b, it will be appreciate that the actual transformer is formed in part by the current coil 122, which constitutes the "primary" winding, while the winding 144a constitutes the secondary winding.

In any event, the core 144b in this embodiment is ferromagnetic. In other embodiments, the core 144b may have other shapes, and/or be formed from other materials. For example, it is known to use a winding 144a about an air core, for example, a Rogowski coil, which may or may not include a casing, for the purpose of measuring current. In this embodiment, the core 144b has a central opening 202 through which the line current carrying conductor (e.g. the current coil 122a) passes. The schematic 205 shows the equivalent circuit for the winding 144a, which in this embodiment has an inductance L of 200 H and a resistance $R_T$. The resistance $R_T$ of the coil is a function of temperature, and in this embodiment is approximate 100Ω at room temperature.

The bias circuit 146 in this embodiment includes a DC voltage source 204, a burden resistor 206, a first resistor 208 and a second resistor 210. The winding 144a includes a first terminal 212 and a second terminal 214. The first terminal 212 of the winding 144a is coupled to the processing circuit 115 via the A/D conversion unit 112. The burden resistor 206 is coupled between the first terminal 212 and reference node 216. The voltage source 204, which may suitably be a 3.3 volt DC source, is coupled between the reference node 216 and circuit ground. The first resistor 208 is coupled between the second terminal 214 of the winding 144a and the reference node 216, and the second resistor 210 is coupled between the second terminal 214 of the winding 144a and circuit ground.

In this embodiment, the burden resistor 206 is 1.2Ω, the first resistor is 10Ω, and the second resistor is 320Ω. In operation, the bias circuit 146 cooperates with the current transformer 144 to produce the current measurement signal IA having two basic components. As discussed above in connection with FIG. 2, the first component, $IA_{AC}$, is an AC component that is representative of the current level flowing through the current coil 122, and the second component is a DC component, $IA_{DC}$. It will be appreciated that the signal IA, although representative of current, is a voltage signal that is representative of the detected current. The burden resistor 206 provides the known function of translating a current signal into a voltage signal representative of the current signal.

In normal operation, current flows through the current coil 122 in accordance with electricity usage by the customer or load 60. It is this value that the meter 100 is intended to measure to generate energy consumption information for billing purposes and like. The current flowing through the current coil 122 is coupled onto the winding 144a via the normal operation of the current transformer 144. Because the winding 144a may include on the order of 1000 turns, and because the current coil 122 represents a single "turn", the coupled current on the winding 144a is scaled down approximately three orders of magnitude. The resulting AC current forms the AC current component of the signal on the winding 144a. The burden resistor 206 provides a voltage drop that essentially converts the AC current component into an AC voltage representative of the AC current. The resulting component forms the AC component $IA_{AC}$ of the measurement signal IA that is provided to the A/D conversion circuit 112. It will be appreciated that in this embodiment, the DC voltage source 204 sets the reference level of the AC voltage component to 3.3 volts, which is configured to ensure that the instantaneous voltage of the AC voltage component is properly within the range of the A/D conversion unit 112.

In addition, a DC circuit is formed through winding 144a via the DC voltage source 204, the burden resistor 206 and the second resistor 210. It will be appreciated that the A/D conversion unit 112 and processing circuit 115 have an impedance exceeding 10 kΩ, and preferably is closer to 50 kΩ, and may therefore be approximated as an open circuit for the DC voltage. The first resistor 208, which has a much smaller resistance than the winding 144a, effectively divides the DC bias voltage from the DC voltage source 204 with the second resistor 210. In this embodiment, the 3.3 VDC bias voltage is dropped 0.1 volt over the 10Ω first resistor 208, and 3.2 volts over the 320Ω second resistor 210. Thus, a similar is 0.1 VDC voltage drop occurs across the burden resistor 206 and winding 144a. A small but measurable amount of this voltage is dropped over the burden resistor 206. This forms the DC component of the output signal, $IA_{DC}$, expressed by the following:

$$IA_{DC} = V_{bias} - (V_{bias} - V_{R2})\left(\frac{R_B}{R_B + R_T}\right) \quad (1)$$

where $IA_{DC}$ is the DC voltage component of the measurement signal provided to the A/D converter, $V_{bias}$ is the DC voltage provided by the DC voltage source 204, $V_{R2}$ is the voltage at the second terminal 214, $R_B$ is the resistance of the burden resistor, and $R_T$ is the temperature-dependent resistance of the winding 144a. It will be appreciated that the component $IA_{DC}$ is a voltage component, but is representative of DC current through the winding, in the same manner that $IA_{AC}$ is a voltage signal that is representative of current through the current coil 122. Referring again to equation (1), it will also be appreciated that the value of $V_{R2}$ can be approximated by:

$$V_{R2} \cong V_{bias}\left(\frac{R_{210}}{R_{208} + R_{210}}\right) \quad (2)$$

Thus, it can be see that the output DC voltage component is a function of $R_T$, which in turn is a function of the temperature of the winding 144a. As a consequence, the bias circuit 146 cooperates with the winding 144a to generate DC voltage component of the signal IA provided to the A/D conversion unit 112 that is dependent upon temperature.

The A/D conversion unit 112 samples the output signal IA from the bias circuit 146 and provides the digitized output signal to the processing circuit 115. The processing circuit 115 receives the digitized output signal, and using normal digital filtering means, separates the DC voltage component of IA from the AC voltage component of IA. The processing circuit 115 uses the digital AC voltage component to calculate energy consumption as discussed above in connection with FIG. 1. The processing circuit 115 uses the digital DC voltage component to calculate resistance for the purposes, and further processing, discussed above in connection with FIG. 1.

Thus, the exemplary bias circuit 146 of FIG. 2 applies a DC voltage across the winding 144a in a continuous manner which allows the processing circuit 115 to calculate resistance of the winding 144a either continuously, or on a periodic basis. In this embodiment, the processing circuit 115 may compare the DC component $IA_{DC}$ directly to the first threshold (temperature), second threshold (open circuit), and low threshold (short circuit) based on initial calibration of the meter 100. For example, when the meter 100 is initially (or subsequently) calibrated, the DC voltage component $IA_{DC}$ may be measured over controlled conditions. From this baseline, the first threshold value may be determined using the temperature at which it is desired to signal a temperature event. For example, if it is desired to detect events of 200° C. above the baseline condition, then the equations (1) and (2), along with the temperature/resistance relationship of copper (or other material of the winding), can be used to determine the $IA_{DC}$ value that represents the first threshold. The second threshold may be set to a much higher level, for example, one that corresponds to 1000° C., and the low threshold may be set to a much lower level, for example, one that corresponds to −200° C. These thresholds may be stored in the memory 120 during meter calibration. In such a case the processing circuit 115 would retrieve these values for the purposes of comparing measured $IA_{DC}$ to the thresholds during normal operation.

In this embodiment, the processing circuit 115 need not specifically determine the resistance (or the temperature) during normal operation, because the thresholds are set for comparison directly to the DC voltage component of the current measurement signal IA. In some cases, the processing circuit 115 nevertheless periodically stores either $IA_{DC}$ or a resistance and/or temperature value derived from $IA_{DC}$, in the memory for later access.

In some cases, the application of a DC voltage across the windings 144a, 154a can cause inaccuracies in the measurement of current by those windings. In particular, the applied DC voltage can cause saturation of the cores 144b, 154b, which affects the accuracy of the AC current detection by the corresponding transformer 144, 154. In the embodiment of FIG. 2, the DC component is kept very small (e.g. 0.1 VDC) to reduce the possibility and/or impact of saturation.

Figure 3:
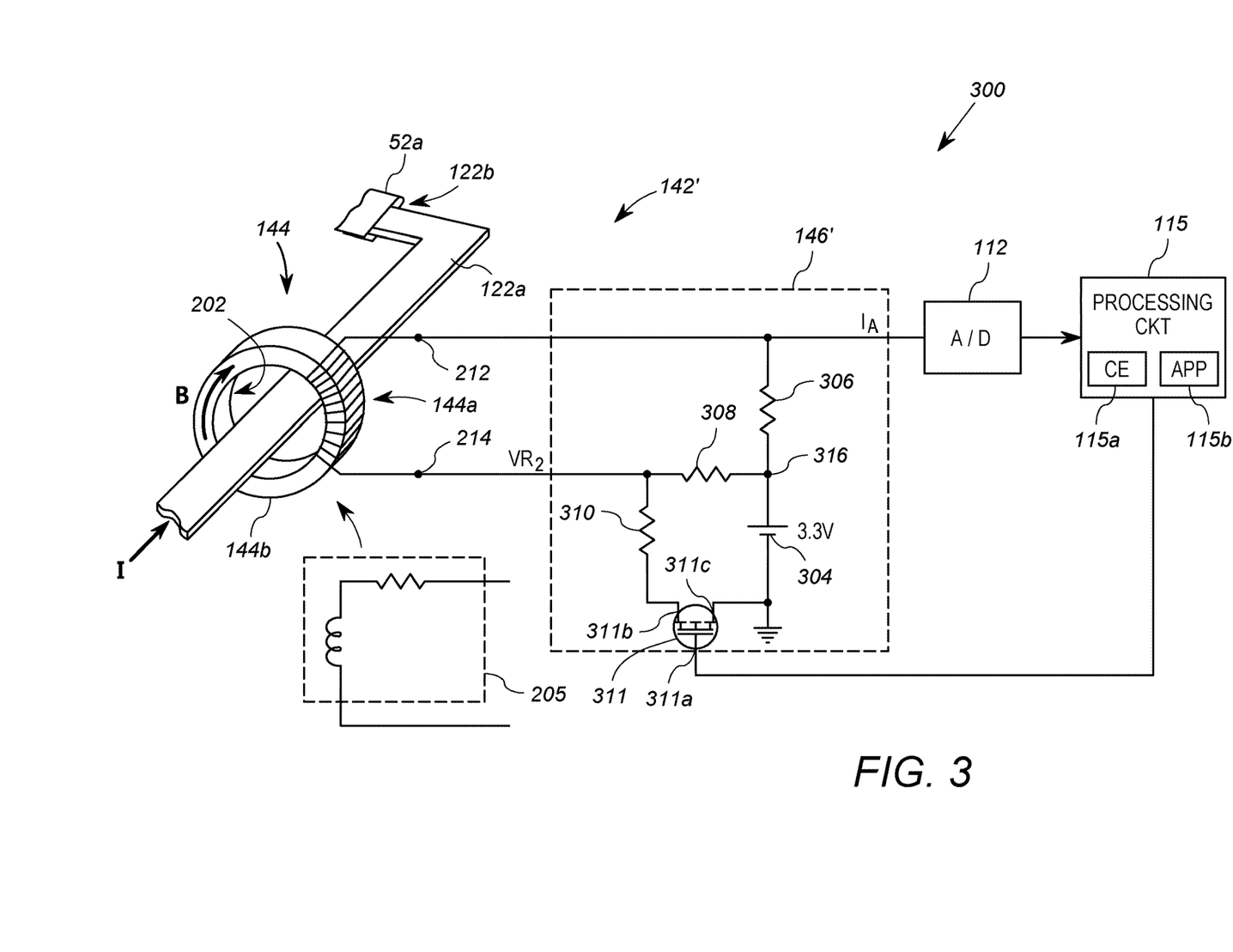
FIG. 3 shows a schematic block diagram of an alternative arrangement for determining temperature information that may be used in the meter of FIG. 1.

Nevertheless, FIG. 3 shows an alternative embodiment that further reduces or eliminates the possibility of inaccuracy of saturation by using a controllable switch to only periodically connect the DC voltage across the windings 144a, 154a. Specifically, FIG. 3 shows an arrangement 300 that may be used as the arrangement 101 of FIG. 1. In contrast the embodiment of FIG. 3, the DC voltage is intermittently applied across the windings 144a, 154a. For example, the arrangement 300 may cause application of a DC voltage for only 250 milliseconds every minute, or even every five to fifteen minutes. Thus, any impact to the AC measurement is substantially reduced. As a result, the actual DC voltage applied may be higher than that used in the circuit of FIG. 2, which can allow for a more accurate resistance measurement.

With specific reference to FIG. 3, the arrangement 300 monitors a current coil connection that may be used as the arrangement 101 of FIG. 1. Like elements of FIGS. 1, 2 and 3 employ like reference numbers. The current transformer 144 has the structure and operation as that discussed above in connection with FIGS. 1 and 2. Thus, the winding 144a in this embodiment has an inductance L of 200 H and a resistance $R_T$ that is a function of temperature. The arrangement of FIG. 3 includes a current sensor 142' that includes the current transformer 144 and the bias circuit 146'. The current sensor 142' is coupled within the meter 100 in the same manner as the current sensor 142 of FIG. 2.

The bias circuit 146' in this embodiment includes a DC voltage source 304, a burden resistor 306, a first resistor 308, a second resistor 310, and a switching device 311. As discussed above in connection with FIG. 2, the winding 144a includes a first terminal 212 and a second terminal 214. The first terminal 212 of the winding 144a is coupled to the processing circuit 115 via the A/C conversion circuit 112. The burden resistor 306 is coupled between the first terminal 212 and reference node 316. The voltage source 304, which may suitably be a 3.3 volt DC source, is coupled between the reference node 316 and circuit ground. The first resistor 308 is coupled between the second terminal 214 of the winding 144a and the reference node 316, and the second resistor 310 is coupled between the second terminal 214 of the winding 144a and circuit ground.

The switching device 311, which may suitable be a FET transistor or other semiconductor device, includes a control terminal 311a, a first terminal 311b and a second terminal 311c. The switching device 311 is configured to controllably and alternately allow current flow, and prevent current flow, between the first terminal 311b and the second terminal 311c. In general, the switching device 311 is configured to controllably operably connect and disconnect the DC voltage source across the winding 144a. To this end, in this embodiment, the first terminal 311b is coupled to the resistor 310 and the second terminal 311c is coupled to ground, such that the resistor 310 is coupled to ground via the first terminal 311b and the second terminal 311c. The control terminal 311a is operably connected to receive control signals from the processing circuit 115.

In this embodiment, the burden resistor 306 is 1.2Ω, the first resistor is 10Ω, and the second resistor is 20Ω. In operation, the bias circuit 146' cooperates with the current transformer 144 to produce the current measurement signal IA having the AC component $IA_{AC}$ that is representative of the current level flowing through the current coil 122, and the second component that is the DC component, $IA_{DC}$.

As with the embodiment of FIG. 2, in normal operation, current flows through the current coil 122 in accordance with electricity usage by the customer or load 60. The current flowing through the current coil 122 is inductively coupled onto the winding 144a by the normal operation of the current transformer 144. The winding 144a is used to generate the AC component of the signal on the winding 144a. The burden resistor 306 provides a voltage drop that essentially converts the AC current component into an AC voltage component $IA_{AC}$ of the measurement signal IA that is provided to the A/D conversion circuit 112. The DC voltage source 304 sets the reference level of the AC voltage component to 3.3 volts, which is configured to ensure that the instantaneous voltage of the AC voltage component is properly within the range of the A/D conversion circuit 112.

In addition, when the switch 311 is closed (or "conducting"), a DC circuit is formed through winding 144a via the DC voltage source 304, the burden resistor 306, the second resistor 310, and the terminals 311b, 311c of the switching device 311. As with the embodiment of FIG. 2, the A/D conversion unit 112 and processing circuit 115 have an equivalent impedance that well exceeds 10 kΩ, and is preferably about 50 kΩ, and may therefore be approximated as an open circuit for the DC voltage. The first resistor 308, which has a much smaller resistance than the winding 144a, effectively divides the DC bias voltage from the DC voltage source 304 with the second resistor 310. In this embodiment, the 3.3 VDC bias voltage is dropped 1.1 volt over the 10Ω first resistor 308, and 2.2 volts over the 20Ω second resistor 310. Thus, a similar is 1.1 VDC voltage drop occurs across the burden resistor 306 and winding 144a. A small but measurable amount of this 1.1 VDC is dropped over the burden resistor 306. This forms the DC component of the output signal, $IA_{DC}$, which is described by equation (1), set forth again below:

$$IA_{DC} = V_{bias} - (V_{bias} - V_{R2})\left(\frac{R_B}{R_B + R_T}\right) \quad (1)$$

where $IA_{DC}$ is the DC voltage component of the measurement signal provided to the A/D converter, $V_{bias}$ is the DC voltage provided by the DC voltage source 304, $V_{R2}$ is the voltage at the second terminal 214, $R_B$ is the resistance of the burden resistor 306, and $R_T$ is the temperature-dependent resistance of the winding 144a. It will be appreciated that the component $IA_{DC}$ is a voltage component, but is representative of DC current through the winding, in the same manner that $IA_{AC}$ is a voltage signal that is representative of current through the current coil 122. Referring again to equation (1), it will also be appreciated that the value of $V_{R2}$ can be approximated by:

$$V_{R2} \cong V_{bias}\left(\frac{R_{310}}{R_{308} + R_{310}}\right) \quad (2)$$

Thus, it can be see that the output DC voltage component is a function of $R_T$, which in turn is a function of the temperature of the winding 144a. As a consequence, the bias circuit 146' cooperates with the winding 144a to generate DC voltage component of the signal IA provided to the A/D conversion unit 112 that is dependent upon temperature.

However, it will be appreciated that when the switch 311 is open (i.e. non-conductive from terminal 311b to 311c), essentially no DC voltage is dropped across the winding 144a. As a consequence, the DC voltage component $IA_{DC}$ of the signal IA is given the following simplification of Equation (1):

$$IA_{DC} = V_{bias} - (V_{bias} - V_{bias})\left(\frac{R_B}{R_B + R_T}\right) \quad (3)$$

$$IA_{DC} = V_{bias} - 0 \quad (4)$$

Thus, when the switching device 311 is open, the DC component does not vary as a function of temperature because no voltage is dropped across the winding 144a. The DC component in this case is merely the DC bias employed for the convenience of the A/D conversion unit 112.

Regardless of whether the switching device 311 is open or closed, the A/D conversion unit 112 samples the output signal IA from the bias circuit 146' and provides the digitized output signal to the processing circuit 115. The processing circuit 115 receives the digitized output signal, and using normal digital filtering means, separates the DC voltage component of IA from the AC voltage component of IA. The processing circuit 115 uses the digital AC voltage component to calculate energy consumption as discussed above in connection with FIG. 1. The processing circuit 115 uses the digital DC voltage component to calculate resistance for the purposes, and further processing, discussed above in connection with FIG. 1. In this embodiment, the processing circuit 115 preferably only attempts to calculate of the winding 144a in a time period surrounding when the switching device 311 is closed.

In further detail of the embodiment of FIG. 3, the processing circuit 115 preferably includes a compute engine function 115a and an application function 115b. In general, the compute engine function ("CE") 115a performs the high speed sample-by-sample calculations for individual, sequential, time intervals. For example, the CE 115a may calculate energy, reactive energy, $V^2$ and $I^2$, among other things, based on samples received over a 250 millisecond interval. The CE 115a provides the resulting "interval data" to the application function 115b after the end of each interval. The application function 115b then uses the interval data to perform further high level processing of the data to generate the accumulated energy consumption data, the RMS voltage, RMS current, and billing-related calculations, among other things. The application function 115b also may control display, storage, and communication functions. In general, the CE function may be based on an implementation of the commercially available metering chip, such as the Teridian 71M6513. It will be appreciated that the CE 115a and application function 115b may be implemented on a single processor, or multiple processors.

Figure 4:
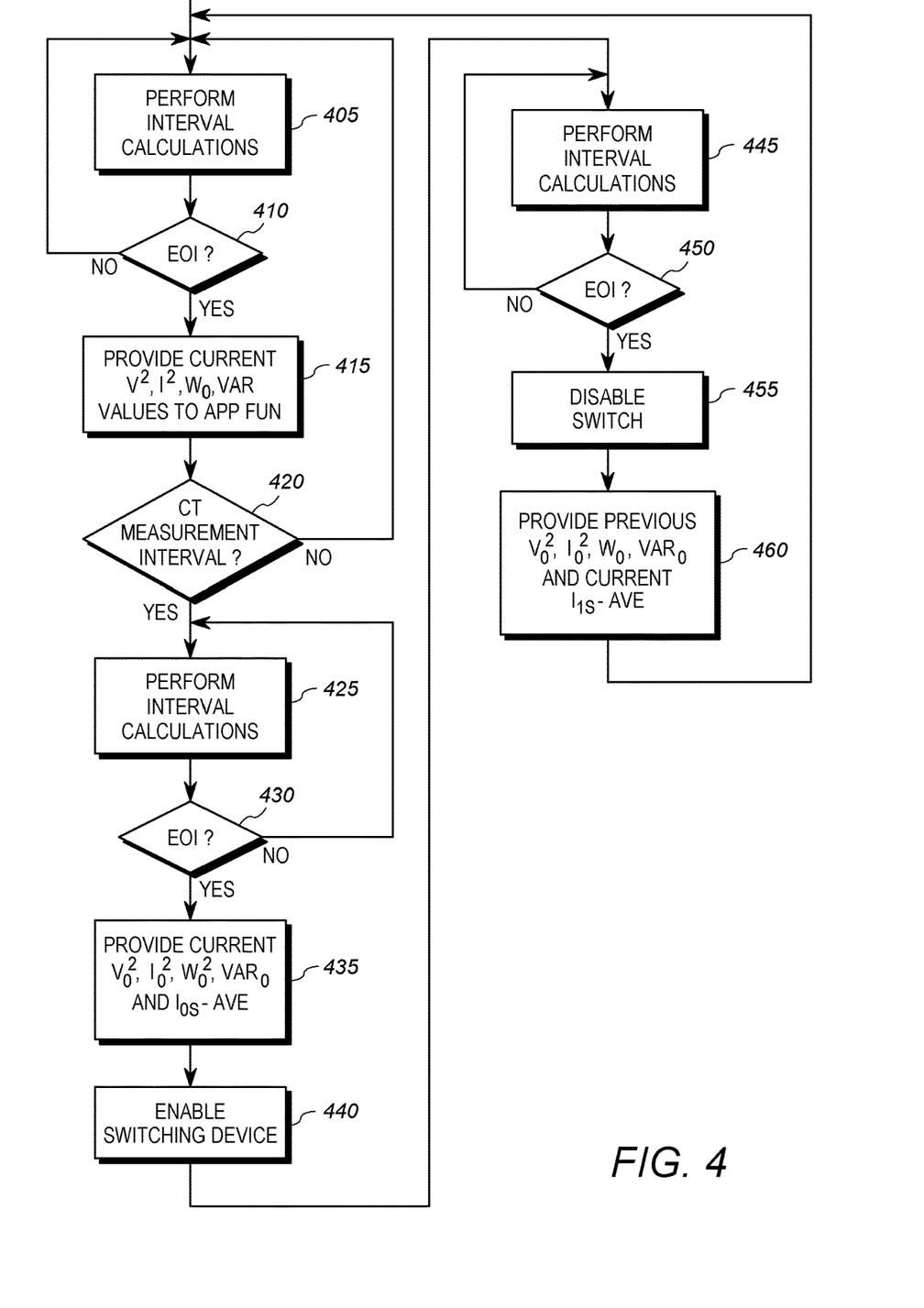
FIG. 4 shows a flow diagram of an exemplary set of operations of a first function of a processing circuit of the arrangement of FIG. 3.
Figure 5:
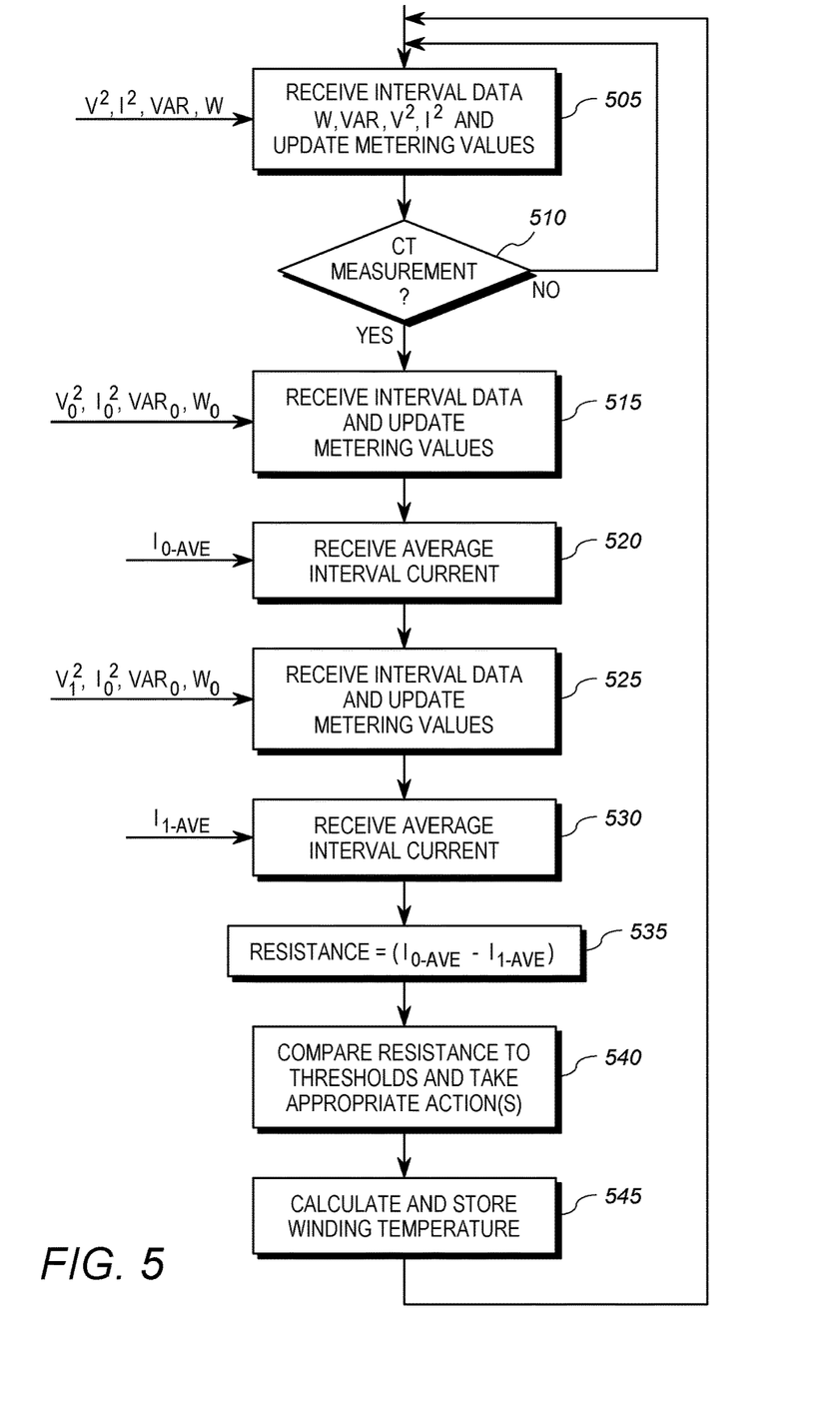
FIG. 5 shows a flow diagram of an exemplary set of operations of a second function of the processing circuit of the arrangement of FIG. 3.

FIGS. 4 and 5 illustrate how, respectively, the CE 115a and application function 115b cooperate to perform resistance calculations in accordance with one exemplary implementation of the arrangement 300 of FIG. 3.

FIG. 4 shows a flow diagram of the representative operations of the CE 115a of the processing circuit of FIG. 3. In general, the CE 115a performs high speed raw energy, reactive energy, $V^2$ and $I^2$ calculations on the incoming samples, which may be sampled at a rate of 2,500 samples per second. As discussed above, the energy calculations are based on summing the product of contemporaneous samples of IA and VA, and VAR-h calculations are based on summing the product of IA samples and corresponding 90° time-shifted VA samples. In general, the CE 115a performs these calculations for all the samples received in a predetermined interval, such as 250 milliseconds, and then transfers the raw calculated values to the application function 115b. Typically, for each new interval, the CE 115a resets all of the running values to zero.

Referring now specifically to FIG. 4, in step 405, the CE 115a (i.e. the processing circuit 115 executing the computer code that carries out the CE function) performs its normal interval calculations of energy (W), reactive energy (VAR), $I^2$ and $V^2$ on an ongoing basis as IAD and VAD samples received from the A/D conversion unit 112. In step 410, the CE 115a determines whether the present interval has ended. If not, then the CE 115a returns to step 405. If so, however, then the CE 115a proceeds to step 415. In step 415, the CE 115a provides the W, VAR, $I^2$ and $V^2$ values of the just completed interval to the application function 115b.

The CE 115a then determines if it is time for sensor winding resistance measurement in step 420. As discussed above, the sensor winding resistance measurements occur periodically, such as once every minute or up to once every fifteen minutes. If it is time for sensor winding resistance measurement, the CE 115a proceeds to step 425. If not, then the CE 115a resets the values W, VAR, $I^2$ and $V^2$ and returns to step 405 to continue the new interval's calculations.

In step 425, the process of determining the resistance information begins within the CE 115a. Specifically, in step 425, the CE 115a continues to calculate the normal interval values W, VAR, $I^2$ and $V^2$, which are designated for convenience as $W_0$, $VAR_0$, $I_0^2$ and $V_0^2$ for the current interval n=0. In addition, the CE 115a calculates an average current value $I_{0\text{-}ave}$ over the interval. To this end, the CE 115a averages the current samples of IAD over the interval. The average current value $I_{0\text{-}ave}$ represents the DC component $IA_{DC}$ of the signal IA. It will be appreciated that because the switch 311 has not yet been closed, the DC component measured in step 425 represents the "baseline" or normal DC component $IA_{DC}$ of the signal IA.

In step 430, the CE 115a determines whether the current interval has ended. If not, then the CE 115a continues in step 425. If so, however, then the CE 115a proceeds to step 435. In step 435, the CE 115a provides the $W_0$, $VAR_0$, $I_0^2$ and $V_0^2$ values of the current (i.e. just completed) interval to the application function 115b. The CE 115a then proceeds to step 440.

In step 440, the CE 115a enables the switch 311. As a consequence, the bias circuit 146' applies the DC voltage across the winding 144a. As a result, the DC component $IA_{DC}$ of IA changes as a function of the resistance of the winding 144a. Because the resistance of the winding 144a varies as a function of temperature, the DC component $IA_{DC}$ now contains a value that is representative of temperature (absent a short or open condition), as discussed above in connection with Equation (1). In step 445, the CE 115a performs calculations of the next interval, $W_1$, $VAR_1$, $I_1^2$ and $V_1^2$, and also calculates the average current for the new interval $I_{1\text{-}ave}$, which differs from the $I_{0\text{-}ave}$ by a value indicative of the resistance of the winding 144a.

In step 450, the CE 115a determines whether the current interval has ended. If not, then the CE 115a returns to step 445. If so, however, then the CE 115a proceeds to step 455. In step 455, the CE 115a disables the switch 311. The CE 115a then proceeds to step 460. In step 460, the CE 115a provides the values $W_0$, $VAR_0$, $I_0^2$ and $V_1^2$ as well as the average current $I_{1\text{-}ave}$ value, to the application function 115b. Thus, it is noted that the CE 115a provides the data from the interval n=0 for W, VAR and $I^2$, instead of the data for the just completed interval n=1. This re-use of the prior interval's data for energy, reactive energy and current addresses any issues relating to temporary saturation of the core 144b of the transformer 144 while the DC voltage was being applied across the winding 144a (i.e. while the switch 311 was closed). The use of the previous interval's energy, reactive energy and current values defines a type of interpolation. Because energy usage typically does not vary greatly in a 250 millisecond interval, reusing a prior interval's data forms a relatively accurate approximation of the next interval's data. By contrast, the error introduced by core saturation due to DC loading of the transformer 144 can cause a greater error. Thus, using the "interpolated" data reduces error.

After step 460, the operations of the CE 115a associated with the resistance measurement of the winding 144a are completed. The CE 115a then returns to step 405 and repeats the entire process in an ongoing manner.

FIG. 5 shows a flow diagram of the corresponding operations of the application function ("AF") 115b of FIG. 3. It will be appreciated that operations of FIG. 5 may be carried out in a variety of ways, and need not follow the exact sequence illustrated. The operations of FIG. 5 employ the various values provided by the CE 115a discussed above.

In step 505, the AF 115b receives the W, VAR, $I^2$ and $V^2$, for a completed interval, and updates various metering calculations using the received data. For example, the values W and VAR for the interval may be added to corresponding running totals that are used for billing and other purposes. The values $I^2$ and $V^2$ may be employed to generate RMS current and voltage calculations. The AF 115b may also cause one or more of the updated metering calculations to be displayed on the display 130.

In step 510, the AF 115b determines if a CT measurement is occurring in the next interval. It will be appreciated that the AF 115b may determine this based on a clock function or from signals received from the CE 115a. In some cases, the AF 115b determines if a CT measurement is occurring based on the fact that it is receiving an average current value $I_{0\text{-}ave}$ that it normally does not receive. In any event, if a CT measurement is not occurring, then the AF 115b returns to step 505 to await the next interval's data. If, however, the AF 115b determines that a CT measurement is occurring, then the AF 115b performs the operations of step 515.

In step 515, the AF 115b receives the $W_0$, $VAR_0$, $I_0^2$ and $V_0^2$ values for the current interval n=0, and updates various metering calculations using the received data. This operation is substantially identical to that of step 505. In addition, in step 520, the AF 115b receives the average current value $I_{0\text{-}ave}$ over the interval.

In step 525, the AF 115b receives the values for the next interval, n=1. However, as discussed above, in the interval n=1, the CE 115a provides some values from the prior interval n=0 as an extrapolation of those values for the interval n=1. The reason for the extrapolation is that there is a significant risk that the current measurement-based values, $W_1$, $VAR_1$, $I_1^2$, may have non-trivial error due to core saturation of the transformer 144 due to the application of the DC voltage by the bias circuit 146. The extrapolation uses, for only the single interval, the values of the previous interval. For intervals of less than a second, and likely even higher, the error introduced by the extrapolation will like be less than error due to core saturation. Accordingly, in step 525, the AF 115b receives for the interval n=1, the values $W_0$, $VAR_0$, $I_0^2$ and $V_1^2$, and updates various metering calculations using the received data. This operation is otherwise substantially identical to that of step 505. In addition, in step 530, the AF 115b receives the average current value $I_{1\text{-}ave}$ over the interval.

Thereafter, in step 535, the AF 115b determines the resistance value of the winding 144a using the following relationship:

$$R_T = k(I_{0\text{-}ave} - I_{1\text{-}ave}), \quad (5)$$

where k is a constant developed based on the voltage applied over the winding 144a.

Once the resistance $R_T$ is determined, the AF 115b in step 540 compares the value $R_T$ to the thresholds associated with a) winding temperature, b) open winding, and c) shorted winding. Specifically, the AF 115b compares the value $R_T$ to the first threshold, the second threshold, and the low threshold, discussed above. If any of those thresholds are exceeded, then the AF 115b stores, displays and/or communicates an indication of the determination/event as discussed above.

After the comparisons, the AF 115b proceeds to step 545. In step 545, the AF 115b calculates a temperature value $T_W$ for the winding 115b. To this end, the memory 120 stores a reference temperature and a reference resistance, as well as the temperature/resistance relationship of the winding.

$$T_W = T_B + \frac{\frac{R_T}{R_B} - 1}{C_T} \quad (6)$$

wherein $R_B$ is the resistance of the winding at the baseline temperature $T_B$, and $C_T$ is the resistance-temperature coefficient of the material of the winding. Thus, for example, the memory may store a baseline resistance $R_B$ of 100Ω for a winding at $T_B$ of 25° C. Copper (the material of the winding 144a) has a resistance temperature coefficient $C_t$ of 3,930 ppm/C. Thus, the AF 115b converts the measured resistance to temperature using the following implementation of Equation (6)

$$T_W = 25 + \frac{\frac{R_T}{100} - 1}{3,930 * 10^{-6}} \quad (7)$$

The AF 115b may suitably store the determined temperature in the memory 120, and may include a time stamp or otherwise be associated with a time and date. It will be appreciated that the one or more of the values $R_B$, $T_B$, $C_T$ may be stored in the memory 120 as part of the program (e.g. AF 115b), or as a separate value retrieved from memory during execution of the AF 115b.

After step 545, the AF 115b returns to step 505.

Thus, the exemplary embodiment of FIGS. 3, 4 and 5 can not only determine winding temperature, which may be used to detect an increase of temperature on the meter socket connection, but also detect open or short circuited windings on the current transformers 144, 154 without disrupting the accuracy of the meter measurements. To this end, the use of the switching device 311 to only apply the DC voltage across the winding 144a (or 154a) for one short duration (under 1 s) in a much longer period (1 to 15 minutes and up). The embodiment of FIGS. 3, 4 and 5 further reduce inaccuracy due to core saturation by extrapolating the current-based measurements for that interval.

In alternative embodiments, the closing of the switching device 311 for measurement purposes occurs as a result of a command received by the processing circuit 115. For example, the processing circuit 115 could receive a command to measure the temperature (via the change in coil resistance) from the communication circuit 121, which, in turn, may suitably have received the command from an external device, not shown. In such a case, the closed switch operations of FIGS. 4 and 5 occur responsive to receiving such a command. The results of the measurements may also be communicated via the communication circuit 121 to an external device, such as to a portable computer or centralized computer of the utility.

Figure 6:
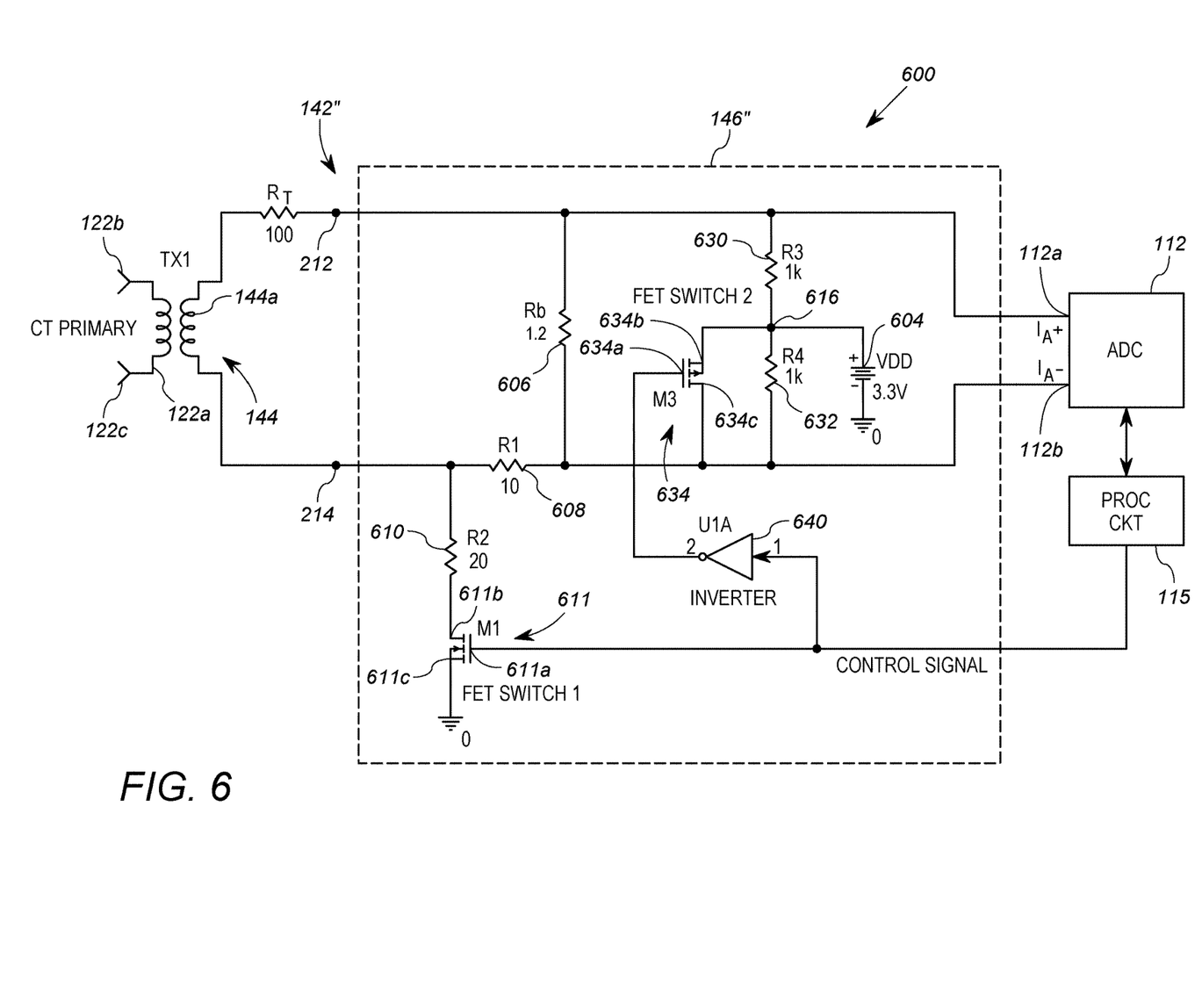
FIG. 6 shows a schematic drawing of another alternative embodiment an arrangement for determining temperature information that employs a differential current measurement.

Another embodiment of an arrangement 600 for monitoring a current coil connection (such as the meter jaw connection 52a/122b) is shown schematically in FIG. 6. In FIG. 6, the arrangement 600 is implemented in another form of current sensor 142" that generates a differential current measurement signal $IA_+$ and $IA_-$. The current sensor 142" may be suitably employed and connected within the meter 100 of FIG. 1 in the place of either or both of the current sensors 142, 152.

In the arrangement 600, the differential current measurement signal component $IA_+$ includes a differential DC component $IA_{DC+}$ and the component $IA_-$ includes a differential DC component $IA_{DC-}$. In general, the A/D conversion unit 112 and processor 115 may suitably determine the DC component $IA_{DC}$ using the averages of the digital different values in a manner similar that described above in connection with FIGS. 4 an 5.

Referring specifically to the arrangement 600, similar to the arrangement 300 of FIG. 3, a DC voltage is intermittently applied across the windings 144a, 154a. For example, the arrangement 600 may cause application of a DC voltage for only 250 milliseconds every minute, or even every five to fifteen minutes. Thus, any impact to the AC measurement is substantially reduced.

The arrangement 600 monitors a current coil connection that may be used as the arrangement 101 of FIG. 1. Like elements of FIGS. 1, 2 and 3 employ like reference numbers. The current transformer 144 has the structure and operation as that discussed above in connection with FIGS. 1 and 2. Thus, the winding 144a in this embodiment has an inductance L of 200 H and a resistance $R_T$ that is a function of temperature.

The bias circuit 146" in this embodiment includes a DC voltage source 604, a burden resistor 606, a first resistor 608, a second resistor 610, differential resistors 630, 632, a first switching device 611, and a second switching device 634. As discussed above in connection with FIG. 2, the winding 144a includes a first terminal 212 and a second terminal 214. The first terminal 212 of the winding 144a is coupled to a first differential input 112a of A/D conversion circuit 112, and the second terminal 214 of the winding 144a is coupled to a second differential input 112b of the A/D conversion circuit 112 via the first resistor 608.

The burden resistor 606 is coupled between the first differential input 112a and the second differential input 112b. The voltage source 604, which may suitably be a 3.3 volt DC source, is coupled between a reference node 616 and circuit ground. The first differential resistor 630 couples the node 616 to the first differential input 112a, and the second differential resistor 632 couples the node 616 to the second differential input 112b.

The switching device 634, which may suitable be a p-channel MOSFET or other semiconductor device, includes a control terminal 634a, a first terminal 634b and a second terminal 634c. The switching device 634 is configured to controllably and alternately allow current flow, and prevent current flow, between the first terminal 634b and the second terminal 634c. In general, the switching device 634 is configured to controllably bypass the second differential resistor 632 to connect the DC voltage source 604 directly to the second differential input 112b. To this end, in this embodiment, the first terminal 634b is coupled to the node 616 and the second terminal 634c is coupled to the second differential input 112b, such that the resistor 632 is effectively bypassed. Closing of the switch effectively applies a DC voltage to the winding 144a via the first resistor 608.

The switching device 611, which may suitably be an n-channel MOSFET or other semiconductor device, includes a control terminal 611a, a first terminal 611b and a second terminal 611c. The switching device 611 is configured to controllably and alternately allow current flow, and prevent current flow, through the second resistor 610. To this end, in this embodiment, the first terminal 611b is coupled to the second resistor 610, which in turn is connected to the second terminal 214 of the winding 144a, the second terminal 611c is coupled to ground. The control terminal 611a of the switching device 611 is also operably coupled to receive the control signal from the processing circuit 115.

The first resistor 608 is serially (and directly) connected between the second terminal 214 of the winding 144a and the second differential input 112b of the AD conversion circuit 112. The second resistor 610 is connected between the second terminal 214 and the first terminal 611b of the switching device 611. In this embodiment, the same control signal is provided to the switches 611, 634. However, the control signal is provided to the control terminal 634a of the switch 634 in this embodiment through an inverter 640 because the switch 634 in this embodiment is a p-channel MOSFET. In other embodiments where the switch 634 is an n-channel MOSFET, the inverter 640 would not be necessary. It will be appreciated through the discussion below that regardless of the types of switches employed, the switches 611, 634 should be in a conducting state when measuring resistance (intermittently) and should be in a non-conducting state when in normal non-measuring operation.

In this embodiment, the burden resistor 606 is 1.2Ω, the first resistor 608 is 10Ω, and the second resistor 610 is 20Ω. In operation, the bias circuit 146" cooperates with the current transformer 144 to produce the differential current measurement signal $IA_+$, $IA_-$ having the AC component $IA_{AC}$ that is representative of the current level flowing through the current coil 122, and the second component that is the DC component, $IA_{DC}$.

As with the embodiment of FIG. 2, in normal operation, current flows through the current coil 122 in accordance with electricity usage by the customer or load 60. The current flowing through the current coil 122 is inductively coupled onto the winding 144a by the normal operation of the current transformer 144. The voltage source 604 and the differential resistors 630, 632 bias the first and second terminals 212, 214 about 3.3 volts DC. The burden resistor 606 provides a voltage drop that essentially converts the AC current component into differential AC voltage components $IA_{AC+}$, $IA_{AC-}$ of the differential measurement signal $IA_+$, $IA_-$ that is provided to the A/D conversion circuit 112.

In addition, when the switches 611 and 634 are conducting, a DC circuit is formed through winding 144a via the DC voltage source 604, the resistor 608, and the second resistor 610. As with the embodiment of FIG. 2, the A/D conversion unit 112 and processing circuit 115 have an equivalent impedance that well exceeds 10 kΩ, and is preferably about 50 kΩ, and may therefore be approximated as an open circuit for the DC voltage. The first resistor 608, which has a much smaller resistance than the winding 144a, effectively divides the DC bias voltage from the DC voltage source 604 with the second resistor 610. In this embodiment, the 3.3 VDC bias voltage is dropped 1.1 volt over the 10Ω first resistor 608, and 2.2 volts over the 20Ω second resistor 310. Thus, a similar is 1.1 VDC voltage drop occurs across the burden resistor 606 and winding 144a. A small but measurable amount of this 1.1 VDC is dropped over the burden resistor 606. This forms the DC component of the output signal, $IA_{DC+}$, $IA_{DC-}$, which is described by equation (8), set forth below:

$$IA_{DC+} - IA_{DC-} = V_{bias} - (V_{bias} - V_{R2})\left(\frac{R_B}{R_B + R_T}\right) \quad (8)$$

where $IA_{DC+}$, $IA_{DC-}$ are the DC voltage components of the measurement signal provided to the A/D converter, $V_{bias}$ is the DC voltage provided by the DC voltage source 604, $V_{R2}$ is the voltage at the second terminal 214, $R_B$ is the resistance of the burden resistor 606, and $R_T$ is the temperature-dependent resistance of the winding 144a. It will be appreciated that the differential components $IA_{DC+}$, $IA_{DC-}$ are voltage components representative of DC current through the winding 144a. Referring again to equation (8), it will also be appreciated that the value of $V_{R2}$ can be approximated by:

$$V_{R2} \cong V_{bias}\left(\frac{R_{610}}{R_{608} + R_{610}}\right) \quad (9)$$

Thus, it can be see that the output DC voltage component is a function of $R_T$, which in turn is a function of the temperature of the winding 144a. As a consequence, the bias circuit 146" cooperates with the winding 144a to generate DC voltage component of the signal IA provided to the A/D conversion unit 112 that is dependent upon temperature.

However, it will be appreciated that when the switches 611, 634 are non-conductive, essentially no DC voltage is dropped across the winding 144a, similar to the embodiment of FIG. 3. Thus, when the switching devices 611 and 634 are non-conductive, the DC component does not vary as a function of temperature because no DC voltage is dropped across the winding 144a.

Regardless of whether the switching devices 611, 634 are conducting or non-conducting, the A/D conversion unit 112 samples the output signal $IA_+$, $IA_-$ from the bias circuit 146" and provides the digitized output signal to the processing circuit 115. The processing circuit 115 receives the digitized output signal, and using normal digital filtering means, separates the DC voltage component of IA from the AC voltage component of IA. The processing circuit 115 uses the digital AC voltage component to calculate energy consumption as discussed above in connection with FIG. 1. The processing circuit 115 uses the digital DC voltage component to calculate resistance for the purposes, and further processing, discussed above in connection with FIG. 1. In this embodiment, the processing circuit 115 preferably only attempts to calculate of the winding 144a in a time period surrounding when the switching devices 611, 634 are conducting.

It will be appreciated that the above-described embodiments are merely illustrative, and that those of ordinary skill in the art may readily develop their implementations and modifications that incorporate the principles of the present invention and fall within the spirit and scope thereof.

I claim:

1. An arrangement for use in a utility meter, comprising:
a meter blade coupled to a current coil;
a current sensor including a winding about a core, the current sensor in a current sensing relationship with the current coil, the winding having a resistance that varies as a function of temperature;
a processing circuit operably coupled to receive a measurement signal from the winding, the processing circuit configured to:
determine a DC component of the measurement signal;
determine the resistance of the winding based at least in part on the determined DC component; and
cause a value representative of the determined resistance to be displayed or communicated to an external device.

2. The arrangement of claim 1, further comprising:
a DC application circuit configured to apply a DC voltage across the winding.

3. The arrangement of claim 2, wherein the DC application circuit includes:
a DC voltage source operably connected across the winding to apply at least one volt DC to the winding.

4. The arrangement of claim 3, wherein the DC application circuit includes a switch configured to connect and disconnect the DC voltage source across the winding.

5. The arrangement of claim 4, wherein the processing circuit is configured to control the switch.

6. The arrangement of claim 1, wherein the processing circuit is further configured to determine the resistance of the winding based in part on a comparison of the determined DC component and a previously-determined DC component of the measurement signal.

7. The arrangement of claim 1, wherein the value representative of the determined resistance is a temperature measurement value representative of a temperature of the winding, and wherein the processing circuit is further configured to determine the temperature measurement value based in part on the determined resistance.

8. The arrangement of claim 5, wherein:
the DC voltage across the winding corresponds to the DC component in the measurement signal; and
the DC application circuit further comprises a burden resistor coupled from a first terminal of the winding to a first reference node, a first resistor serially coupled between the second terminal of the winding and the first reference node, and a second resistor having a first side coupled to the second terminal of the winding and a second side coupled to be at a reference voltage; and
the DC voltage source is operably connected between the first reference node and the reference voltage to provide a DC voltage to the first reference node.

9. The arrangement of claim 8, wherein the switch is configured to open and close a circuit from the second terminal of the winding to the reference voltage through the second resistor.

10. The arrangement of claim 9, further comprising a second switch operably coupled to controllably and operably disconnect a first path from the DC voltage to the first reference node such that a voltage other than the DC voltage is provided to the first reference node.

11. The arrangement of claim 10, wherein:
the DC voltage is configured to provide the DC voltage to a second reference node;
the first path extends from the first reference node to the second reference node; and
further comprising,
a third resistor serially coupled from the second reference node to the first terminal, and
a fourth resistor serially coupled from the second reference node to the first reference node in parallel to the first path.

12. The arrangement of claim 11, wherein a resistance value of the second resistor exceeds a resistance value of the first resistor, and the resistance value of the first resistor exceeds a resistance value of the burden resistor.

13. The arrangement of claim 9, wherein a resistance value of the second resistor exceeds a resistance value of the first resistor, and the resistance value of the first resistor exceeds a resistance value of the burden resistor.

14. The arrangement of claim 2, wherein:
the winding comprises a first terminal and a second terminal;
the DC voltage across the winding corresponds to the DC component in the measurement signal; and
the DC application circuit further comprises a burden resistor coupled from a first terminal of the winding to a first reference node, a first resistor serially coupled between the second terminal of the winding and the first reference node, and a second resistor having a first side coupled to the second terminal of the winding and a second side coupled to be at a reference voltage; and
a DC voltage source is operably connected between the first reference node and the reference voltage to provide a DC voltage to the first reference node.

15. The arrangement of claim 14, wherein a resistance value of the second resistor exceeds a resistance value of the first resistor, and the resistance value of the first resistor exceeds a resistance value of the burden resistor.

16. The arrangement of claim 1, further comprising a display operably connected to the processing circuit.

17. An arrangement for use in a utility meter, comprising:
a meter blade coupled to a current coil;
a current sensor including a winding about a core, the current sensor in a current sensing relationship with the current coil, the winding having a resistance that varies as a function of temperature;
a processing circuit operably coupled to receive a measurement signal from the winding, the processing circuit configured to:
determine a DC component of the measurement signal;
determine the resistance of the winding based at least in part on the determined DC component; and
store a value representative of the determined resistance.

18. The arrangement of claim 17, further comprising a DC application circuit that includes:
a DC voltage source operably connected across the winding to apply at least approximately one volt DC to the winding.

19. The arrangement of claim 18, wherein the DC application circuit includes a switch, the switch configured to controllably operably connect and disconnect the DC voltage source across the winding.

* * * * *